United States Patent [19]
Wolters et al.

[11] Patent Number: 5,319,124
[45] Date of Patent: Jun. 7, 1994

[54] PROCESS FOR THE PREPARATION OF DIALKYL CARBONATES

[75] Inventors: Erich Wolters, Cologne; Heinz Landscheidt, Duisburg; Alexander Klausener, Stolberg; Lothar Puppe, Burscheid, all of Fed. Rep. of Germany

[73] Assignee: Bayer Aktiengesellschaft, Leverkusen, Fed. Rep. of Germany

[21] Appl. No.: 23,303

[22] Filed: Feb. 26, 1993

[30] Foreign Application Priority Data

Mar. 2, 1992 [DE] Fed. Rep. of Germany ....... 4206527

[51] Int. Cl.$^5$ ............................................. C07C 69/96
[52] U.S. Cl. ..................................... 558/260; 558/277
[58] Field of Search ........................................ 558/277

[56] References Cited

U.S. PATENT DOCUMENTS

| | | | |
|---|---|---|---|
| 4,879,401 | 11/1989 | Doumaux, Jr. et al. | 558/488 |
| 5,235,087 | 8/1993 | Klausener et al. | 558/260 |

FOREIGN PATENT DOCUMENTS

| | | |
|---|---|---|
| 04251975 | 5/1991 | European Pat. Off. |
| 3834065 | 4/1990 | Fed. Rep. of Germany |
| 4020941 | 1/1992 | Fed. Rep. of Germany |
| 60-75447 | 4/1985 | Japan |
| 60-94943 | 5/1985 | Japan |

OTHER PUBLICATIONS

Chin. Sci. Bull 34 (1989), 875–876.
Platinum Metals Review 34 (1990), 178–180.

*Primary Examiner*—José G. Dees
*Assistant Examiner*—Dwayne C. Jones
*Attorney, Agent, or Firm*—Sprung Horn Kramer & Woods

[57] ABSTRACT

Dialkyl carbonates can be prepared by the reaction of carbon monoxide with alkyl nitrites in a continuous gas phase reaction, using a platinum metal catalyst on an amorphous alumosilicate having a content of 30-80 atom% Al, based on the sum of Al and Si, as a support, which catalyst may optionally comprise additional material of a compound of antimony, bismuth, aluminium, copper, vanadium, niobium, tantalum, tin, iron, cobalt, nickel or a mixture of a plurality of these, and hydrogen halide being added in the course of the reaction intermittently or continuously. In this reaction, the dialkyl carbonates are formed with almost quantitative selectivity; the corresponding dialkyl oxalates cannot be detected in most cases.

20 Claims, No Drawings

PROCESS FOR THE PREPARATION OF DIALKYL CARBONATES

BACKGROUND OF THE INVENTION

1. Field of the Invention

The present invention relates to a process for the preparation of dialkyl carbonates by the reaction of carbon monoxide (CO) with alkyl nitrites in the presence of a catalyst from the group of the platinum metal halogenides on a support of amorphous alumosilicate, which may contain additional compounds of further elements.

Dialkyl carbonates are of general chemical significance. For example, diethyl carbonate is an excellent solvent in the medium boiling point range. Furthermore, the dialkyl carbonates are excellent carbonylation and acylation reagents. Finally, they are very important in the preparation of other carbonates, of urethanes and of ureas.

2. Description of the Related Art

Known preparations of dialkyl carbonates involve the reactions of phosgene or of alkyl chloroformates with alcohols. However, there is an increasing interest in replacing the use of the toxic phosgene or of the intermediate products derived therefrom, such as the chloroformic esters, by other processes. In addition to attempts to obtain dialkyl carbonates by reacting CO with lower alcohols, processes of particular importance are those in which CO is reacted in the gas phase with alkyl nitrite on a platinum metal catalyst. In reactions of this type, in addition to the desired dialkyl carbonate, dialkyl oxalate is always detected.

Thus, EP 425 197 discloses a process which, according to its preferred embodiment, leads to dialkyl carbonates of methanol or ethanol from CO and methyl or ethyl nitrite in the gas phase on a PdCl$_2$ catalyst on activated carbon. The selectivities in obtaining the desired lower dialkyl carbonates, according to said EP 425 197, Table 1, reach levels of up to 94%; however, lower dialkyl oxalates and CO$_2$ are always observed as by-products. Moreover, when this work was repeated, the high selectivities quoted could not be reproduced satisfactorily. The catalysts of said EP 425 197 contain additions of chlorides of base metals; a considerable addition of hydrogen chloride, namely an amount of 1 to 50 mol%, based on the platinum metal in the catalyst, is added to the system, or part of the catalyst has to be withdrawn from the reactor and subjected to a treatment with hydrogen chloride.

In the Journal for Catalytic Research (China), Vol. 10 (1), (1989) pp. 75–78, too, the support used for a PdCl$_2$-containing catalyst comprises charcoal, producing dimethyl carbonate from CO and methyl nitrite, but in each case dimethyl oxalate is also produced.

A Pd/charcoal catalyst is also mentioned in Chin. Sci. Bull. 34 (1989), 875–76 for the preparation of dimethyl carbonate from CO and methyl nitrite.

This preference for a charcoal support is not surprising, since it is reported in Platinum Metals Review 34 (1990), 178–180, referring to older literature, that in the reaction of a lower alkyl nitrite with CO on a Pd catalyst, depending on the support, different main products are obtained; according to this article, a charcoal support predominantly yields the dialkyl carbonates, while an oxidic support such as, for example, an Al$_2$O$_3$ support primarily yields dialkyl oxalates.

SUMMARY OF THE INVENTION

It has now been found that amorphous alumosilicates as the catalyst support not only, surprisingly, yield the dialkyl carbonates if CO is reacted with alkyl nitrites, but additionally also give rise to a significant increase of the selectivity in producing the desired dialkyl carbonates, so much so that, in addition to more than 97% selectivity, in many cases more than 99% selectivity in producing said dialkyl carbonates, in general no oxalate at all can be detected. Only a small amount of CO$_2$ can be observed in the reaction mixture. Furthermore, the use of amorphous alumosilicates as a support, which use had been considered to be impossible, provides the essential advantage of increased stability and abrasion resistance, compared to a supported catalyst based on a charcoal support.

A process has been found for the preparation of dialkyl carbonates of the formula $$O=C(OR)_2 \qquad (I)$$

in which

R represents straight-chain or branched C$_1$–C$_4$-alkyl, by reacting carbon monoxide (CO) with alkyl nitrites of the formula $$RONO \qquad (II)$$

in which

R has the indicated meaning, in the presence or absence of an inert gas and in the presence or absence of the alcohol ROH on which the compounds are based, and in the presence or absence of NO, on a supported catalyst comprising platinum metal, at elevated temperature in a continuous gas phase reaction, which is characterised in that, as the support, amorphous alumosilicates having a content of 30–80 atom% Al, based on the sum of Al and Si, are used, the platinum metal is present in the form of a halogenide or a halogenide-containing complex compound, where the platinum metal halogenide or the halogen-containing complex containing the platinum metal can be formed in situ in the process reactor from the platinum metal or a halogen-free platinum metal compound with the aid of hydrogen halogenide under the reaction conditions, the catalyst is further equipped or not equipped with an addition of a compound of antimony, bismuth, aluminium, copper, vanadium, niobium, tantalum, tin, iron, cobalt, nickel or a mixture of a plurality of these, and the process is carried out using a volume ratio of nitrite: CO=0.1–10:1 and at a temperature from 50°–150° C., hydrogen halogenide being resupplied intermittently or continuously in at least that amount which is discharged, even if no hydrogen halogenide is added, from the reactor with the reaction mixture.

DETAILED DESCRIPTION OF THE INVENTION

Amorphous alumosilicates to be used as supports according to the invention are mixtures of Al$_2$O$_3$ and SiO$_2$ in widely fluctuating proportions, some of which mixtures have the characteristics of compounds. The proportion of Al is 30–80 atom%, preferably 50–75 atom%, based on the sum of Al and Si. Alkali metal oxides or alkaline earth metal oxides may be present in proportions, for example, in the range of 0.01–30% by weight, based on the total weight of the amorphous alumosilicate. When used according to the invention, they have BET areas of 100-1000 m²/g, preferably 200-800 m²/g.

Alumosilicates of this type are found as natural raw materials, but they can also be prepared synthetically by coprecipitation of $Al_2O_3$ and $SiO_2$ from solutions of aluminate and silicate. A typical representative is $Al_2O_3 \cdot SiO_2$. By means of drying and calcination, the surface of amorphous alumosilicates can be varied in a manner familiar to those in the art. As the specific surfaces increase, the amorphous alumosilicates increasingly acquire acidic properties. Such alumo-silicates with acidic properties are preferred according to the invention.

The reaction in the process according to the invention proceeds according to the following reaction equation:

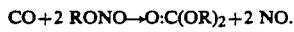

$$CO + 2\ RONO \rightarrow O{:}C(OR)_2 + 2\ NO.$$

Examples of straight-chain or branched alkyl having 1-4 C atoms include methyl, ethyl, propyl, isopropyl, butyl, isobutyl, said n-alkyls being preferred, methyl and ethyl being particularly preferred, and methyl being especially preferred.

In principle it is possible to start from a mixture of different alkyl nitrites, which does, however, give rise to a mixture of different dialkyl carbonates and possibly unsymmetrically substituted dialkyl carbonates. In order to achieve a uniform reaction it is therefore preferred to start from just one alkyl nitrite.

While it is possible, in principle, to react CO with an alkyl nitrite without any further components of the mixture, for example if the composition of the mixture is outside the explosive limits, an inert gas is nevertheless often used to dilute the reactants. Examples of inert gases include noble gases, nitrogen and carbon dioxide, preferably argon, nitrogen or carbon dioxide, particularly preferably nitrogen and carbon dioxide. The amount of the inert gas is from 20 to 80% by volume, preferably from 30 to 70% by volume, based on the total gas volume to be fed into the reactor. The inert gas and any unreacted residual amounts of the reactants, which it may contain, can be recycled.

The volume ratio of the reactants nitrite and CO to one another is 0.1-10:1, preferably 0.2-4:1, particularly preferably 0.3-3:1.

The gas mixture to be reacted may further contain small amounts of alcohol ROH, for example in an amount of 0-10% amount of 0-10% by volume, both based on the total volume of the gas mixture to be used. Such additions of ROH and/or NO may, for example, result from the preparation of the alkyl nitrite and may, for example, be introduced into the reaction gas mixture together with said alkyl nitrite.

The catalyst for the process according to the invention is applied to the amorphous alumosilicates as supports; its reactive component, when in the reactive state, comprises the platinum metal halogenide or the complex compound containing platinum metal halogenide. Such complex compounds are basically known and, for example, are alkali metal chloride complex compounds, such as lithium or sodium tetrachloropalladate, $Li_2[PdCl_4]$ or $Na_2[PdCl_4]$.

It has further been found that the platinum metal halogenide or the complex compound containing the platinum metal halogenide can be formed in situ in the reactor from metallic platinum metal or a halogen-free platinum metal compound under the reaction conditions, i.e. in the presence of the gas mixture to be reacted, with the aid of hydrogen halogenide. It is therefore possible to charge the reactor with an otherwise comparable catalyst, which initially contains the platinum in metallic form or which had been prepared with the aid of a halogen-free platinum metal compound. Such possible halogen-free platinum metal compounds include, for example, platinum metal nitrates, propionates, butyrates, carbonates, oxides, hydroxides or others known to those skilled in the art.

Elements from the group of the platinum metals in the context of the invention are palladium, platinum, iridium, ruthenium and rhodium, preferably palladium, ruthenium and rhodium, particularly preferably palladium.

Halogenides in the context of the invention are fluoride, chloride, bromide and iodide, preferably chloride and bromide, particularly preferably chloride.

The amount of the platinum metal halogenide or of the complex compound containing the platinum metal halogenide is 0.01-8% by weight, preferably 0.05-4% by weight calculated as platinum metal and based on the total weight of the catalyst.

The catalyst for the process according to the invention is or is not further equipped with an addition of a compound of antimony, bismuth, aluminium, copper, vanadium, niobium, tantalum, tin, iron, cobalt, nickel or of a mixture of a plurality thereof; in a preferred embodiment such an addition is present. Such additions are present in the form of a salt, or in the metallic form of said elements. In a similar way as has been described above for the platinum metal, the metallic form of said additions together with hydrogen halogenide under the reaction conditions forms, for example, the halogenide form of such additions. In a preferred embodiment, such additions comprise a compound of antimony, bismuth, aluminium, vanadium, niobium, tantalum or a mixture of a plurality thereof. In a particularly preferred embodiment, said additions are present as halogenides of antimony, bismuth, aluminium, vanadium, niobium or tantalum, and especially preferred are the chlorides of antimony, bismuth, aluminium, vanadium, niobium and tantalum.

The amount of the addition is 0.1-100 times, preferably 0.2-10 times the amount of platinum metal, calculated as metal, both for the addition and for the platinum metal.

The preparation of a catalyst to be used according to the invention is carried out by methods which in principle are known to those in the art. For example, the support can be impregnated or sprayed with a solution of one of said platinum metal compounds. This also applies to the said addition or additions. In the case where the platinum metal is to be fixed on the support as a metal or in the form of the carbonate, oxide or hydroxide, and is to be activated only in the reactor in the manner described with the aid of hydrogen halogenide under the reaction conditions to give the platinum metal halogenide, the platinum metal compound applied can be reduced to the metal in a manner known to those skilled in the art by a suitable reducing agent, or can be converted by a suitable precipitant into the carbonate, oxide or hydroxide.

It has further been found that, in order to achieve uniformly high selectivities for dialkyl carbonate, it is advantageous to bring hydrogen halogenide into contact with the catalyst during the course of the latter's useful life. During this process is was observed that, in principle, the yield increases with greater amounts of hydrogen halogenide. Thus, the concentration of hydrogen halogenide (e.g. HCl) which is supplied to the catalyst along with the feedstock, may for example be up to 1000 ppm. It was, however, further found that said amount of hydrogen halogenide can be considerably smaller. Thus it is only necessary to replace the amount of hydrogen halogenide discharged along with the reaction products, which derives from the activated form of the catalyst. This amount can be determined analytically. In general, it varies within a range from 1 to 2,000 µg of hydrogen halogenide per g of dialkyl carbonate formed. In order to simplify the working-up procedure, it may be desirable to use hydrogen halogenide sparingly.

Hydrogen halogenide in the context of the invention is hydrogen fluoride, hydrogen chloride, hydrogen bromide and hydrogen iodide, preferably hydrogen chloride and hydrogen bromide, particularly preferably hydrogen chloride.

The hydrogen halogenide may be metered as such, in the form of a gas, into the reaction mixture. It is, however, also possible to meter it in as a solution in one of the substances present in the reaction mixture, for example as a solution in the alcohol on which the alkyl nitrite is based.

Catalysts of the type described have a long working life (>200 h). In addition to the mechanical stability and abrasion resistance already described, they retain their activity and selectivity for an extraordinarily long time.

Said catalysts can be charged with 700–5,000 l of mixture of the gaseous reactants per l of catalyst and per hour (GHSV).

The method according to the invention is carried out at a temperature from 50° to 150° C., preferably at from 70° to 120° C., particularly preferably at from 70° to 110° C., and at a pressure from 0.8 to 10 bar, preferably at from 1 to 7 bar, particularly preferably at from 1 to 5 bar.

The alkyl nitrites to be used according to the invention are prepared according to known methods, for example from the corresponding alcohol and nitrous acid, which, for example, is formed in situ from an alkali metal nitrite and a mineral acid such as sulphuric acid. The nitrogen monoxide NO formed in the course of the process according to the invention can be regenerated continuously with oxygen and fresh alcohol to give alkyl nitrite (German Offenlegungsschrift 38 34 065) and can be recycled together with unreacted reactants.

EXAMPLES

Catalyst preparation and definitions

COMPARATIVE EXAMPLE 1

100 ml of activated carbon granules were impregnated in a known manner with an aqueous solution of $PdCl_2$ and $CuCl_2$, and the product was dried at 80° C. under reduced pressure (20 torr). The finished catalyst contained 8 g of Pd/l and 8 g of Cu/l.

The space time yield (STY) in [g/l.h] and for dimethyl carbonate in the examples is calculated according to $$\frac{m_{DMC}}{V_{Cat} \cdot t}$$

where $m_{DMC}$ is the amount of dimethyl carbonate (DMC) formed, $V_{Cat}$ is the catalyst volume, and t is the time.

The selectivity S (%) is calculated according to $$S = \frac{n_{DMC}}{N_{DMC} + 2 \times n_{DMC} + n_{MF} + n_{FDA}} \times 100 \, [\%]$$

where
$n_{DMC}$ = Quantity of dimethyl carbonate
$n_{DMO}$ = Quantity of dimethyl oxalate
$n_{MF}$ = Quantity of methyl formate
$n_{FDA}$ = Quantity of formaldehyde dimethyl acetal.

EXAMPLE 1

100 ml of $Al_2SiO_5$ bodies (alumosilicate of the approximate composite $Al_2O_3.SiO_2$ having a specific surface of 700 m²/g; PY 700 from Kali-Chemie) were impregnated with an aqueous $Li_2PdCl_4$ solution, and the product was dried at 80° C. under reduced pressure (29 torr). The catalyst then contained 8 g of Pd/l.

EXAMPLE 2

A vertically arranged glass tube (length 50 cm, diameter 4 cm) was charged with 20 ml of the catalyst from Example 1 between a packing of Raschig rings.

The glass tube was heated to 90° C., and a gas mixture was passed through, comprising 55% $N_2$, 20% MeONO, 20% CO and 5% MeOH. The space velocity was 800 l/l h. The gas discharged from the reactor was cooled to 5° C., and the condensed phase thus obtained was investigated by means of gas chromatography. The noncondensed products were examined by means of IR spectroscopy and mass spectroscopy.

Dimethyl carbonate was formed after 2 h with a STY of 200 g/l h and selectivity =99%. After 10 hours, the STY was 190 g/l.h and the selectivity was 99%.

COMPARATIVE EXAMPLE 2

The experiment described in Example 2 was repeated, the catalyst used being the product described in Comparative Example 1.

Dimethyl carbonate was formed after 2 h with an STY of 80 g/l h and a selectivity of 97%. After 10 hours, the STY was 60 g/l h, and the selectivity was 75%.

What is claimed is:

1. A process for the preparation of a dialkyl carbonate of the formula

O=C(OR)₂, in which
R represents straight-chain or branched $C_1C_4$-alkyl, by reacting carbon monoxide (CO) with alkyl nitrite of the formula

RONO, in which
R has the indicated meaning,
in the presence or absence of an inert gas and in the presence or absence of the alcohol ROH on which compounds are based, and in the presence or absence of NO, on a supported catalyst comprising platinum metal, at elevated temperature in a continuous gas phase reaction, wherein as the support, an amorphous alumosilicate having a content of 30–80 atom% Al, based on the sum of Al and Si, is used, the platinum metal is present in the form of halogenide or a halogenide-containing complex compound, where the platinum metal halogenide or the halogen-containing complex containing the platinum metal can be formed in situ in the process reactor from the platinum metal or a halogen-free platinum metal compound with the aid of hydrogen halogenide under the reaction conditions, the catalyst is further equipped or not equipped with an addition of a compound of antimony, bismuth, aluminium, copper vanadium, niobium, tantalum, tin, iron, cobalt, nickel or a mixture of a plurality of these, and the process is carried out using a volume ratio of nitrite: CO=0.1-10:1 and at a temperature from 50° to 150° C. and a pressure of from 0.8 to 10 bar, hydrogen halogenide being added intermittently or continuously in at least that amount which is discharged from the reactor with the reaction mixture.

2. The process of claim 1, wherein R represents methyl or ethyl.

3. The process of claim 2, wherein R represents methyl.

4. The process of claim 1, wherein the amorphous alumosilicate as the support has a content of 50-75 atom% Al, based on the sum of Al and Si.

5. The process of claim 1, which is carried out at from 70° to 120° C.

6. The process of claim 5, which is carried out at from 70° to 110° C.

7. The process of claim 1, wherein a volume ratio of nitrite: CO=0.2-4:1 is used.

8. The process of claim 7, wherein a volume ratio of nitrite: CO=0.3-3:1 is used.

9. The process of claim 1, wherein the platinum metal used is selected from the group consisting of palladium, platinum, iridium, ruthenium and rhodium.

10. The process of claim 9, wherein the platinum metal used is selected from the group consisting of palladium, ruthenium and rhodium.

11. The process of claim 1, wherein the platinum metal halogenide used is selected from the group consisting of the simple or complex fluorides, chlorides, bromides and iodides.

12. The process of claim 11, wherein the platinum metal halogenide used is selected from the group consisting of the simple or complex chlorides and bromides.

13. The process of claim 12, wherein the platinum metal halogenide used is a simple or complex chloride.

14. The process of claim 1, wherein the catalyst is equipped with an addition of a compound of antimony, bismuth, aluminium, vanadium, niobium, tantalum or a mixture of a plurality thereof.

15. The process of claim 14, wherein the catalyst is equipped with an addition of an aluminium compound.

16. The process of claim 1, which is carried out in the presence of an inert gas, the inert gas amounting to from 20 to 80% by volume of the total gas volume.

17. The process of claim 16, wherein the inert gas amounts to from 30 to 70% by volume of the total gas volume.

18. The process of claim 1, wherein the catalyst is charged with from 700 to 5,000 l of the mixture of gaseous reactants per hour and per l of catalyst.

19. The process of claim 1, wherein the alumosilicate support has a BET area of 100-1000 m²/g.

20. The process of claim 1, wherein the alumosilicate support has a BET area of 200-800 m²/g.

* * * * *

UNITED STATES PATENT AND TRADEMARK OFFICE
CERTIFICATE OF CORRECTION

PATENT NO. : 5,319,124
DATED : June 7, 1994
INVENTOR(S) : Erich Wolters, et al.

It is certified that error appears in the above-identified patent and that said Letters Patent is hereby corrected as shown below:

Column 6, line 55,     after "with" insert --an--

Signed and Sealed this

Sixth Day of April, 1999

Attest:

Attesting Officer

Q. TODD DICKINSON

Acting Commissioner of Patents and Trademarks